US006168777B1

(12) United States Patent
Greff et al.

(10) Patent No.: US 6,168,777 B1
(45) Date of Patent: *Jan. 2, 2001

(54) METHODS FOR TREATING PROSTATE TUMORS USING RADIOACTIVE COMPOSITIONS

(75) Inventors: Richard J. Greff, St. Pete Beach, FL (US); George Wallace, Coto de Caza, CA (US)

(73) Assignee: Micro Therapeutics, Inc., Irvine, CA (US)

(*) Notice: Under 35 U.S.C. 154(b), the term of this patent shall be extended for 0 days.

This patent is subject to a terminal disclaimer.

(21) Appl. No.: 09/185,147

(22) Filed: Nov. 3, 1998

Related U.S. Application Data

(63) Continuation-in-part of application No. 08/962,819, filed on Nov. 3, 1997.

(51) Int. Cl.$^7$ .................................................. A61K 51/12
(52) U.S. Cl. .................. 424/1.25; 424/1.33; 424/1.29; 424/1.37; 424/1.65; 424/1.61; 600/3; 600/4
(58) Field of Search .................................... 424/1.25, 1.29, 424/1.33, 1.21, 1.37, 1.61, 1.65; 600/3, 4, 7, 8

(56) References Cited

U.S. PATENT DOCUMENTS

| | | |
|---|---|---|
| 3,527,224 | 9/1970 | Rabinowitz et al. . |
| 3,591,676 | 7/1971 | Hawkins et al. . |
| 4,268,495 | 5/1981 | Muxfeldt et al. . |
| 4,795,741 | 1/1989 | Leshchiner et al. . |
| 4,938,763 | 7/1990 | Dunn et al. . |
| 5,443,454 | 8/1995 | Tanabe . |
| 5,514,379 | 5/1996 | Weissleder et al. . |
| 5,580,568 | 12/1996 | Greff et al. . |
| 5,667,767 | 9/1997 | Greff et al. . |
| 5,695,480 * | 12/1997 | Evans et al. .................. 604/264 |
| 5,762,903 * | 6/1998 | Park et al. .................. 424/1.29 |
| 5,942,209 * | 8/1999 | Leavitt et al. .................. 424/1.25 |

FOREIGN PATENT DOCUMENTS

US97/07055 4/1997 (WO).

OTHER PUBLICATIONS

"*CANCER, Principles & Practice of Oncology*", 4th Ed., vol. 1, "*Cancer Treatment*", pp. 545–548 (1993).

Casarett and Doull's *Toxicology*, Amdur, et al., Editors, Pergamon Press, New York, pp. 661–664 (1975).

Castaneda–Zuniga, et al., *Interventional Radiology*, in Vascular Embolotherapy, Part 1, 1:9–32, Williams & Wilkins, Publishers (1992).

Encyclopedia of Medical Devices and Instrumentation, J.G. Webster, Editor (1988) 4:2456.

Hellman, "*CANCER, Principles & Practice of Oncology*", 4th Ed., vol. 1, Chapter 15, "*Principles of Radiation Therapy*", pp. 248–250 (1993).

Kinugasa, et al., "Early Treatment of Subarachnoid Hemorrhage After Preventing Rerupture of an Aneurysm", *J. Neurosurg.*, 83:34–41 (1995).

Kinugasa, et al., "Prophylactic Thrombosis to Prevent New Bleeding and to Delay Aneurysm Surgery", *Neurosurg.*, 36:661 (1995).

Kinugasa, et al., "Direct Thrombosis of Aneurysms with Cellulose Acetate Polymer", *J. Neurosurg.*, 77:501–507 (1992).

Mandai, et al., "Direct Thrombosis of Aneurysms with Cellulose Acetate Polymer", *J. Neurosurg.*, 77:497–500 (1992).

Sitton, "Early and Late Radiation–Induced Skin Alterations Part I:Mechanisms of Skin Changes", *Oncology Nursing Forum*, 19(5):801–807 (1992).

Taki, et al., "Selection and Combination of Various Endovascular Techniques in the Treatment of Giant Aneurysms", *J. Neurosurg.*, 77:37–42 (1992).

\* cited by examiner

*Primary Examiner*—Jose' G. Dees
*Assistant Examiner*—Shahnam Sharareh
(74) *Attorney, Agent, or Firm*—Burns, Doane, Swecker & Mathis, LLP

(57) ABSTRACT

Disclosed are methods for treating solid mass prostate tumors in a male mammal by use of a radiation composition.

12 Claims, No Drawings

METHODS FOR TREATING PROSTATE TUMORS USING RADIOACTIVE COMPOSITIONS

CROSS-REFERENCE TO RELATED APPLICATIONS

This application is a continuation-in-part of U.S. patent application Ser. No. 08/962,819 filed Nov. 3, 1997 which application is incorporated herein by reference in its entirety.

BACKGROUND OF THE INVENTION

1. Field of the Invention

This invention is directed to methods for treating prostate tumors by use of radioactive compositions. Specifically, these methods entail the in vivo delivery of radioactive compositions which are delivered as a fluid to one or more sites in the prostate of a male mammal including the solid mass tumor(s) located on or in the prostate. Subsequent solidification of this composition in the prostate results in delivery of a controlled amount of radiation to the prostate.

In one embodiment, the fluidic radioactive compositions employed in the methods of this invention comprise a biocompatible polymer, a biocompatible solvent and a radioactive agent which provides therapeutic doses of radiation. In another embodiment, the fluidic radioactive compositions employed in the methods of this invention comprise a biocompatible prepolymer, a radioactive agent and optionally a biocompatible solvent which provides therapeutic doses of radiation to the prostate.

References

The following publications are cited in this application as superscript numbers:

1. Dunn, et al., U.S. Pat. No. 4,938,763 for "Biodegradable In-Situ Forming Implants and Methods of Producing Same", issued Jul. 3, 1990
2. Kinugasa, et al., "Direct Thrombois of Aneurysms with Cellulose Acetate Polymer", *J. Neurosurg.*, 77:501–507 (1992)
3. "CANCER, Principles & Practice of Oncology", 4th Ed., Volume 1, "Cancer Treatment", pp. 545–548 (1993)
4. Greff, et al., U.S. Pat. No. 5,667,767, for "Novel Compositions for Use in Embolizing Blood Vessels", issued Sep. 16, 1997
5. Greff, et al., U.S. Pat. No. 5,580,568 for "Cellulose Diacetate Compositions for Use in Embolizing Blood Vessels", issued Dec. 3, 1996
6. Kinugasa, et al., "Early Treatment of Subarachnoid Hemorrhage After Preventing Rerupture of an Aneurysm", *J. Neurosurg.*, 83:34–41 (1995)
7. Kinugasa, et al., "Prophylactic Thrombosis to Prevent New Bleeding and to Delay Aneurysm Surgery", *Neurosurg.*, 36:661 (1995)
8. Taki, et al., "Selection and Combination of Various Endovascular Techniques in the Treatment of Giant Aneurysms", *J Neurosurg.*, 77:37–24 (1992)
9. Evans, et al., U.S. patent application Ser. No. 08/802,252 for "Novel Compositions for Use in Embolizing Blood Vessels", filed Feb. 19, 1997
10. Castaneda-Zuniga, et al., Interventional Radiology, in Vascular Embolotherapy, Part 1, 1:9–32, Williams & Wilkins, Publishers (1992)
11. Rabinowitz, et al., U.S. Pat. No. 3,527,224 for "Method of Surgically Bonding Tissue Together", issued Sep. 8, 1970
12. Hawkins, et al., U.S. Pat. No. 3,591,676 for "Surgical Adhesive Compositions", issued Jul. 6, 1971
13. Nori, et al., Current Issues in Techniques of Prostate Brachytherapy, Seminars in Surgical Oncology, 13:444–453 (1997)
14. Anderson, et al., Spacing Nomograph for Interstitial Implants of 125-I Seeds, Med. Phys., 3:48–51 (1976)

All of the above publications are herein incorporated by reference in their entirety to the same extent as if each individual reference was specifically and individually indicated to be incorporated herein by reference in its entirety.

2. State of the Art

Adenocarcinoma of the prostate is the most common malignancy diagnosed among men in the United States. Current therapeutic regimens for treating prostate tumors include external radiation therapy, brachytherapy, surgery, radical prostatectomy, and the like as well as combinations of two or more of the above.

Brachytherapy, or the internal deposition of radioactive particles into the prostate, has superior potency preservation rates as compared to external beam radiation therapy or surgery. Brachytherapy is characterized as temporary (i.e., radioactive seeds are delivered, e.g., by a catheter to the prostate for a short period of time and then removed) or permanent (i.e., radioactive seeds are delivered to the prostate and not removed). Permanent brachytherapy typically involves needle injection of radioactive seeds into the prostate.[13] The radioactive seeds comprise a radioactive agent, e.g., $^{192}$iridium, typically dimensioned with a length of from 2–4 millimeters. Such seeds are typically injected via a 17 or 18 gage needle into the prostate via stereotactic imaging with the aid of ultrasound or fluoroscopic guidance and the protocol typically entails the delivery of up to 20 or more seeds. Stereotactic imaging allows the clinician to accurately deliver these seeds to the desired location in the prostate and the radiation emitted from these seeds effectively causes necrosis of at least a portion of the tumor over time.

One drawback with such permanent brachytherapy is that the total dose of radiation delivered into the prostate is governed by the size and number of the seeds delivered as well as the radioactive content of the seeds. Typically, the size and radioactive content of the seeds employed is dictated by the commercial availability of the seeds and, accordingly, the clinician typically has control only over the number of seeds delivered as a means to control the total dose of radiation. In certain cases where delivery of a high local dose of radiation to a particular portion of the prostate is desired by the clinician, multiple seed injections in this area will be required.

It is clear, however, that allowing the clinician better control of the radiation dose delivered to the prostate will simplify the protocol and provide greater flexibility in the treatment regimen selected by the clinician.

SUMMARY OF THE INVENTION

This invention is directed to methods for treating prostate tumors by use of radioactive compositions. These compositions are delivered to the prostate as a fluid composition which solidifies in vivo to form a solid, coherent radioactive mass. The methods of this invention permit the clinician to control the total amount of radiation delivered to the prostate during each injection merely by adjusting the quantity of fluid delivered and the concentration of radiation per given volume of fluid. In any event, sufficient amounts of radiation are delivered to the prostate to effect necrosis of at least part of the solid mass tumors located thereon or therein.

Accordingly, in one of its method aspects, this invention is directed to a method for causing necrosis to a portion of a solid mass prostate tumor which method comprises:

(a) selecting a fluidic composition comprising a biocompatible polymer, a biocompatible solvent and a water insoluble radioisotope; and (b) injecting a sufficient amount of said composition into the prostate of a male mammal under conditions wherein a solid mass is formed wherein the radioisotope is employed in an amount effective to cause necrosis of at least a portion of said tumor.

Preferably the radioactive fluid composition employed in this aspect of the methods of this invention comprises:

(a) a biocompatible polymer;

(b) a biocompatible solvent; and (c) from about 0. 1 to about 35 weight percent of a water insoluble radioisotope having a radioactive content of from about 0.50 microcurie to about 200 millicuries.

The biocompatible polymer employed in these compositions and methods can be either a biodegradable polymer or a non-biodegradable polymer but is, preferably, a non-biodegradable polymer.

In another aspect of this invention, the biocompatible polymer can be replaced with a biocompatible prepolymer and, when so used, the presence of the biocompatible solvent becomes optional. In this embodiment, this invention is directed to a method comprising:

(a) selecting a fluidic composition comprising a biocompatible prepolymer, a water insoluble radioisotope and optionally a biocompatible solvent; and (b) injecting a sufficient amount of said composition into the prostate of a male mammal under conditions wherein a solid mass is formed wherein the radioisotope is employed in an amount effective to cause necrosis of at least a portion of said tumor.

Preferably the radioactive fluid composition employed in this aspect of the methods of this invention comprises:

(a) a biocompatible prepolymer;

(b) an optional biocompatible solvent; and (c) from about 0.1 to about 35 weight percent of a water insoluble radioisotope having a radioactive content of from about 0.5 microcurie to about 200 millicurie.

In a preferred embodiment of either of the method aspects, the amount and radioactive content of the radioisotope is sufficient to provide for a cumulative ionizing radiation dosage at the site of implantation in a mammalian subject of from about 1000 to about 20,000 rads [10–200 Gray (Gy)].

It is, of course, understood that both the activity of the radioactive element and dose of radiation delivered to the prostate varies widely due to the requirements of different tumors, tissues, volume of tissue treated, amount of tumor present, etc. Evaluation of such factors to determine the appropriate activity of the radioactive isotope and the dose of radiation delivered are well within the skill of the art.

In a further preferred embodiment of either of the method aspects, the biocompatible solvent is dimethylsulfoxide (DMSO), ethanol or acetone.

In one embodiment, the radioisotope acts as a contrast agent to permit visualization of the composition during catheter delivery. Alternatively, a non-radioactive contrast agent is employed in combination with the radioisotope in order to ensure visualization.

DETAILED DESCRIPTION OF THE INVENTION

This invention is directed to methods for treating prostate tumors in male mammals by use of radioactive compositions which methods entail the in vivo delivery of radioactive compositions which are delivered as a fluid to one or more sites in the prostate. Subsequent solidification of this composition in the tissue results in delivery of a controlled amount of radiation into the prostate.

However, prior to discussing this invention in further detail, the following terms will first be defined:

The term "solid mass tumor" refers to cancerous and non-cancerous conditions manifested by a solid mass growth as opposed to conditions lacking such a solid mass growth, e.g., leukemia. The term "solid mass prostate tumors" refer to solid mass tumors located on or in the prostate gland of male mammals.

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art. [1,3] For example, Dunn, et al.[1] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers and combinations thereof. Other biodegradable polymers include, for example, gelatin, collagen, etc.[3]

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 5 weight percent of the ethylene vinyl alcohol copolymer, 20 weight percent of a tantalum contrast agent in DMSO has a viscosity equal to or less than 60 centipoise at 20° C. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in the methods described therein.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 $\mu$m or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic and substantially non-immunogenic when used internally in the patient and which are substantially insoluble in blood. Suitable biocompatible prepolymers include, by way of example, urethanes, cyanoacrylates[10,11,12], (C1–C6)hydroxyalkyl (C1–C6) alkacrylate (e.g., hydroxyethyl methacrylate), silicone prepolymers, and the like. The prepolymer can either be a monomer or a reactive oligomer[12]. Preferably, the biocompatible prepolymer does not cause an adverse inflammatory reaction when employed in vivo.

The term "radioisotope" refers to naturally or non-naturally occurring water insoluble radioisotopes conventionally employed in nuclear medicine including, by way of example only, $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{52}$magnesium, $^{55}$iron, $^{32}$phosphorus, and $^{90}$strontium. Other radionuclides currently being produced for use in nuclear medicine include, for example, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, and $^{123}$iodine. Each of these isotopes can be made by standard techniques well known in the art[13]. Additionally, radioisotopes which are water soluble or water reactable are typically used as water insoluble salts.

In one embodiment, radioisotopes having a sufficiently high atomic number so as to be radiopaque can be used to serve both as a source of radiation and as a water insoluble contrast agent for detection under fluoroscopy.

In another embodiment, a separate non-radioactive contrast agent is employed in conjunction with the radioisotope.

The term "absorbed dose" or "radiation dose" refers to the dose of radiation typically employed by the attending oncologist in treating solid mass tumors. The radiation dose is defined in terms of energy deposited per unit mass, given in the following units: 1 Gray (Gy)=1 Joule per kilogram. In the past, the standard unit of radiotherapy was 1 rad, and 1 Gy=100 rads.

Compositions

The polymer or prepolymer compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Where a separate non-radioactive contrast agent is employed, sufficient amounts of this contrast agent are then added to the biocompatible solvent to achieve the effective concentration for the complete composition. Preferably, the composition will comprise from about 7 to about 40 weight percent of total contrast agent (non-radioactive contrast agent plus any radiopaque radioisotope) and more preferably from about 14 to about 30 weight percent and even more preferably about 22 weight percent.

The biocompatible solvent preferably comprises from about 40 to about 90 weight percent of the composition based on the total weight of the composition and more preferably about 50 to about 90 weight percent.

When a water soluble non-radioactive contrast agent is employed, the agent is typically soluble in the solution comprising the non-aqueous solvent and stirring is effected to render the composition homogeneous.

When a water insoluble non-radioactive contrast agent is employed, the agent is insoluble in the biocompatible solvent, and stirring is employed to effect homogeneity of the resulting suspension. In order to enhance formation of the suspension, the particle size of the water insoluble non-radioactive contrast agent is preferably maintained at about 10 $\mu$m or less and more preferably at from about 1 to about 5 $\mu$m (e.g., an average size of about 2 $\mu$m).

In one embodiment, a non-radioactive contrast agent having a particle size of less than 10 $\mu$m is prepared, for example, by fractionation. In such an embodiment, a non-radioactive water insoluble contrast agent such as tantalum, having an average particle size of less than about 20 $\mu$m, is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition can be heat sterilized and then stored preferably in sealed bottles or vials until needed.

Each of the polymers recited herein is commercially available or can be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions can be prepared by adding sufficient amounts of any non-radioactive contrast agent employed in the liquid (e.g., liquid prepolymer) to achieve the effective concentration for the complete polymer composition. Preferably, the total contrast agent (non-radioactive contrast agent plus any radiopaque radioisotope) will comprise from about 7 to about 40 weight percent of the prepolymer composition based on the total weight of the composition and more preferably from about 14 to about 30 weight percent and even more preferably about 22 weight percent.

When a non-radioactive contrast agent is used which is not soluble in the biocompatible prepolymer composition, stirring is employed to effect homogeneity of the resulting suspension. In order to enhance formation of the suspension, the particle size of the insoluble non-radioactive contrast agent is preferably maintained at about 10 $\mu$m or less and more preferably at from about 1 to about 5 $\mu$m (e.g., an average size of about 2 $\mu$m).

When the prepolymer is liquid (as in the case of cyanoacrylates or silicone), the use of a biocompatible solvent is not strictly necessary but may be preferred to provide for an appropriate viscosity, for an appropriate curing time, etc. in the composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the total weight of the composition.

Suitable solvents include iodinated soy bean or poppy seed oil for cyanoacrylates and water for hydroxyacrylics such as hydroxyethyl methacrylate. In such cases, the oil acts both as a carrier for the prepolymer, a contrast agent and a polymerization time modifier. Other solvents include hexamethyldisiloxane which is preferably employed in conjunction with silicone.

In a particularly preferred embodiment, the prepolymer is a cyanoacrylate which is preferably employed in a 1:1 ratio with an iodinated oil. When so employed, the cyanoacrylate adhesive is selected to have a viscosity of from about 5 to about 40 centipoise at 20° C.

The radioisotope is preferably added to the otherwise complete composition immediately prior to the administration of the composition to the patient in order to reduce exposure of radiation to the clinician. In a preferred embodiment, the radioisotope is $^{192}$iridium, $^{198}$gold, $^{125}$iodine, $^{137}$cesium or $^{60}$cobalt. The radioisotope is preferably selected relative to the type and size of the solid mass tumor and its location in the patient. This material may also be used as part of or the entire contrast agent to aid in the placement of the composition to cause necrosis to at least a portion of the tumor.

Treatment dosages of radiation employed in a particular patient are, of course, dependent upon the judgment of the attending clinician and nuclear medicine professional depending upon factors such as the type and severity of the solid mass prostate tumor in the patient, the age, weight and general condition of the patient, the toxicity and/or side effects due to the radiation treatment and the like. Such factors are well known to the skilled artisan.

While there is no consensus on the ideal radiotherapy prescription for a particular tumor type, a number of prescriptions are currently used based either on the principle of administering the dose of radiation either over a relatively long treatment time in relatively small fractions or over a short treatment time in relatively large fractions. For example, 64 Gy in 32 fractions over 6.5 weeks or 52 Gy in 15 fractions over 3 weeks. Appropriate prescription is based on an assessment of the individual tumor.

In any event, in this embodiment, sufficient levels of radiation are employed to effect necrosis of at least part of the tumor.

In view of the above, the compositions described herein preferably comprise from about 0.1 to about 35 weight percent of a water insoluble radioisotope having from a radioactive content of from about 0.5 microcurie to about 200 millicurie. In another preferred embodiment, the amount and radioactive content of the radioisotope is sufficient to provide for a cumulative ionizing radiation dosage at the site of implantation in a mammalian subject of from about 1000 to 20,000 rads [10 to 200 Gray (Gy)].

The solid mass formed by the methods of this invention is permanently placed within the patient.

Methods

The compositions described above can be employed in the treatment of solid mass prostate tumors. Prior to treatment, preplanning of the therapeutic protocol is necessary to evaluate the prostate volume, determine the total radiation activity needed to encompass the prostate gland and deliver the appropriate minimum peripheral dose, and to determine the pattern of placement of the radioactive composition in the prostate. Each of these preplanning steps is well known and documented in the art.[13] For example, determination of the prostate volume can be conducted using transrectal ultrasound, computed tomography, and the like. Likewise, determination of total radioactivity and positioning of the seeds can be achieved from software programs described in the art.[14]

Upon completion of the preplanning protocol, injection of the radioactive composition may be performed intraoperatively or percutaneously under conditions well known in the art.[13] In either case, a sufficient amount of this composition is introduced into one or more sites in the prostate using, for example, needle delivery under fluoroscopy so that precipitation of the polymer or polymerization of the prepolymer in the prostate can be visualized.

When the polymeric composition is introduced in vivo, the biocompatible solvent diffuses rapidly into the body fluid and a solid, non-migratory precipitate or solid mass forms which precipitate is the water insoluble polymer and radioisotope encapsulated therein as well as any non-radioactive water insoluble contrast agent. Without being limited to any theory, it is believed that initially, a soft gel to spongy solid precipitate or solid mass forms upon contact with the body fluid.

When a prepolymeric composition is introduced in vivo, the prepolymer rapidly polymerizes in situ (preferably in less than 15 minutes and more preferably in less than 5 minutes) and a solid non-migratory mass forms which mass is the water insoluble polymer and radioisotope encapsulated therein as well as any non-radioactive water insoluble contrast agent.

In either case, a solid non-migratory radioactive mass forms in the prostate which ablates at least a portion of the tumor(s) located therein.

Utility

The compositions described herein are useful in ablating solid mass prostate tumors. When employed, the level of radiation employed in the composition is sufficient to ablate at least a portion of such solid mass prostate tumors. Accordingly, these compositions find use in human male and other male mammalian subjects requiring treatment. It is contemplated that the compositions used in the methods of this invention can also be employed as a carrier for a chemotherapeutic agent wherein this agent is delivered in vivo for subsequent release to the solid mass prostate tumor. Such chemotherapeutic agents are well known in the art and, include by way of example only, fluorouracil, methotrexate, cisplatin and the like. A pharmaceutical agent such as an anti-inflammatory agent, an antibiotic, and the like can be employed either in combination with the chemotherapeutic agent or as an alternative thereto.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc | cubic centimeter |
| DMSO | dimethylsulfoxide |
| EVOH | ethylene vinyl alcohol copolymer |
| g | gram |
| Gy | gray (units for dose of radiation; 1 Gy = 1 J per kg = 100 rads) |
| kg | kilogram |
| mg | milligram |
| mL | milliliter |
| OD | outer diameter |
| ppm | parts per million |
| $\mu$Ci | microCurie |
| $\mu$m | micron |

Example 1

The purpose of this example is to demonstrate the preparation of polymer compositions useful in this invention. These compositions were prepared using "cold" isotopes in order to illustrate the compatibility of the compositions and suitability for delivery in vivo. It is understood that "hot" compositions could be similarly prepared.

Specifically, an EVOH polymer composition was prepared as follows:

Composition 0.396 g EVOH (48 mole percent ethylene);
1.485 g micronized tantalum; and
4.95 mL DMSO.

After dissolution of the polymer at 50° C., 3 cc of this composition was then added to 0.03 g iridium powder (Aldrich Chemical Company, Milwaukee, Wis., USA, Catalog No. 20968-6, 99.9% purity, screened to <25 $\mu$m) to provide for a suspension comprising 0.4% by weight iridium. The resulting composition was then shaken for 4 minutes to disperse the insoluble materials. Immediately, 0.8 cc of the suspension was withdrawn via a 1 cc syringe through a 21 gauge needle. Three 0.1 cc aliquots were then injected into an excess of normal saline maintained at about 37° C. to generate the precipitate. The saline was then stirred for about 10 minutes whereupon the precipitate was examined for inner/outer consistency. In each case, a solid coherent precipitate formed in the saline.

The procedure set forth above was repeated twice. In the first instance, the amount of tantalum powder was changed to 14 weight percent and the amount of iridium powder was increased to 6 weight percent. In the second instance, the tantalum powder was removed from the composition and the amount of iridium adjusted to 20 weight percent. In each case, the total amount of tantalum/iridium was about 20 weight percent.

Both compositions, upon injection into saline, provided a solid coherent precipitate.

Example 2

The purpose of this example is to demonstrate the preparation of a prepolymer composition useful in this invention.

This compositions was prepared using "cold" isotopes in order to illustrate the compatibility of the 20 composition and suitability for delivery in vivo. It is understood that "hot" compositions could be similarly prepared.

Specifically, a cyanoacrylate prepolymer composition was prepared by adding 500 mg of iridium non-radioactive powder (Aldrich Chemical Company, Milwaukee, Wis., USA, Catalog No. 20968-6, 99.9% purity, screened to <25 $\mu$m) to 2 g n-butyl cyanoacrylate containing 100 ppm $SO_2$ as a stabilizer to yield a composition comprising 20% by weight of iridium. The ingredients mixed well, yielding a black/gray suspension. The iridium settled within several seconds after mixing, so constant, gentle agitation was required. In this regard, a higher viscosity cyanoacrylate composition could be used to prolong the suspension time of the iridium or, alternatively, a smaller particle size of the iridium can be used.

The mixture remained liquid with no signs of premature polymerization when evaluated at one hour after mixing and again after 12 days thereby evidencing that the iridium was compatible in this composition.

About 0.2 cc of this composition was taken up in a 1 cc syringe through a 21 gage needle and injected into about 150 cc of an aqueous solution of 0.1 N $NaHCO_3$ to simulate a tissue environment and cure the prepolymer. Upon injection, three small black/gray droplets were formed which immediately fell to the bottom of the container. It took about 15 minutes for the cyanoacrylate to fully cure and to be tack free.

The procedure set forth above was repeated with cyanoacrylate alone (i.e., without the iridium) and the cyanoacrylate cured in approximately the same time evidencing that the iridium was compatible with the cyanoacrylate.

Example 3

The purpose of this example is to illustrate how to deliver the composition of either Example 1 or 2 to the prostate of a male mammal. This example employs a dog with a solid mass tumor.

Specifically, a male dog (25 kg) having a tumor in the prostate gland is selected for use in this example. At this time, 0.10 mL of a 0.4% iridium composition described in Example 1 above (except that the iridium has a radioactive content of 150 $\mu$Ci) is shaken to ensure homogeniety and then loaded into a 1 cc syringe fitted with a 26 gage needle. The tip of the syringe is positioned in the prostate gland of the dog with the aid of ultrasound or fluoroscopy to ensure proper positioning and approximately 0.05 mL of this composition is injected therein. Upon introduction into the prostate, a solid coherent precipitate forms which comprises the polymer, the contrast agent and the iridium which solidifies in the prostate.

After injection, the needle is repositioned into a second site within the prostate, again with the aid of either ultrasound or fluoroscopy, and the remaining 0.05 mL of the radioactive composition is delivered thereto.

Over 30 days, the amount of radiation delivered internally to the prostate of the dog is about 25 Gray.

From the foregoing description, various modifications and changes in the composition and method will occur to those skilled in the art. All such modifications coming within the scope of the appended claims are intended to be included therein.

What is claimed is:

1. A method for causing necrosis to a portion of a solid mass prostate tumor in a male mammal which method comprises:
    (a) selecting a fluidic compositions comprising:
        (i) a biocompatible, non-cross-linked, non-biodegradable polymer which polymer is insoluble in body fluid of a mammal;
        (ii) a biocompatible solvent which is an organic material liquid at least at body temperature of the mammal and which solubilizes said polymer with the proviso that when said solvent comprises water, the amount of water employed is sufficiently small that the dissolved polymer precipitates upon contact with the blood; and
        (iii) a water insoluble radioisotope with the proviso that when the radioisotope is either water soluble or water reactable, said isotope is used as a water insoluble salt
    (b) injecting a sufficient amount of said composition into the prostate of a male mammal under conditions wherein a solid non-migratory precipitate is formed
    wherein the radioisotope is employed in an amount effective to cause necrosis of at least a portion of said tumor.

2. The method according to claim 1 wherein said biocompatible solvent is selected from the group consisting of dimethylsulfoxide, ethanol and acetone.

3. The method according to claim 2 wherein said biocompatible solvent is dimethylsulfoxide.

4. The method according to claim 1 wherein said non-biodegradable biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

5. The method according to claim 4 wherein said non-biodegradable biocompatible polymer is a copolymer of ethylene and vinyl alcohol.

6. The method according to claim 1 wherein said radioisotope is selected from the group consisting of $^{90}$yttrium, $^{192}$iridium, $^{198}$gold, $^{125}$iodine, $^{137}$cesium, $^{60}$cobalt, 55cobalt, $^{56}$cobalt, $^{57}$cobalt, $^{57}$magnesium, $^{55}$iron, $^{32}$phosphorus, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, 62 zinc, $^{61}$copper, $^{201}$thallium, and $^{123}$iodine.

7. The method according to claim 1 which further comprises a non-radioactive contrast agent.

8. The method according to claim 7 wherein said non-radioactive contrast agent is water soluble.

9. The method according to claim 8 wherein said water soluble non-radioactive contrast agent is selected from the group consisting of metrizamide, iopamidol, iothalamate sodium, iodomide sodium, and meglumine.

10. The method according to claim 7 wherein said non-radioactive contrast agent is water insoluble.

11. The method according to claim 10 wherein said water insoluble contrast agent is tantalum, tantalum oxide, barium sulfate, tungsten, gold and platinum.

12. The method according to claim 1 wherein said fluidic composition comprises from about 0.1 to about 35 weight percent of a water insoluble radioisotope having from a radioactive content of from about 0.5 microcurie to about 200 millicurie.

* * * * *